(12) United States Patent
Burkett et al.

(10) Patent No.: US 9,895,108 B2
(45) Date of Patent: Feb. 20, 2018

(54) PRESSURE SENSING INTRAVASCULAR DEVICES WITH REDUCED DRIFT AND ASSOCIATED SYSTEMS AND METHODS

(71) Applicant: Volcano Corporation, San Diego, CA (US)

(72) Inventors: David H. Burkett, Temecula, CA (US); Douglas E. Meyer, Folsom, CA (US)

(73) Assignee: VOLCANO CORPORATION, San Diego, CA (US)

( * ) Notice: Subject to any disclaimer, the term of this patent is extended or adjusted under 35 U.S.C. 154(b) by 730 days.

(21) Appl. No.: 14/014,842

(22) Filed: Aug. 30, 2013

(65) Prior Publication Data

US 2014/0066790 A1 Mar. 6, 2014

Related U.S. Application Data

(60) Provisional application No. 61/695,955, filed on Aug. 31, 2012.

(51) Int. Cl.
*A61B 5/02* (2006.01)
*A61B 5/00* (2006.01)
(Continued)

(52) U.S. Cl.
CPC ........ *A61B 5/6851* (2013.01); *A61B 5/02154* (2013.01); *A61M 25/09* (2013.01);
(Continued)

(58) Field of Classification Search
None
See application file for complete search history.

(56) References Cited

U.S. PATENT DOCUMENTS 5,228,453 A * 7/1993 Sepetka ............... A61M 25/09
600/434
6,062,089 A 5/2000 Ichihashi
(Continued)

FOREIGN PATENT DOCUMENTS

| WO | WO 01/13779 | 3/2001 |
|---|---|---|
| WO | WO 2010/030882 A1 | 3/2010 |
| WO | WO 2012/093266 | 7/2012 |

OTHER PUBLICATIONS

"Hardness Scale—Durometer Comparisons of Materials", Plastics International, http://www.plasticsintl.com/polhardness.htm, retrieved Nov. 18, 2016.*
(Continued)

*Primary Examiner* — Navin Natnithithadha
*Assistant Examiner* — Michael R Bloch

(57) ABSTRACT

Intravascular devices, systems, and methods are disclosed. In some embodiments, the intravascular devices include at least one pressure sensing component positioned within a distal portion of the device. In some instances, a plurality of conductors are electrically coupled to the pressure sensing component and a potting material covers the electrical connections between the plurality of conductors and the pressure sensing component. In some instances, the potting material has a durometer hardness between about 20 Shore A and about 50 Shore A, a moisture absorption rate of about 0% per twenty-four hours, a linear shrinkage of 0%, a coefficient of thermal expansion (m/m/-° C.) of between about $1.0 \times 10^{-5}$ and about $5.0 \times 10^{-4}$, and a volume resistivity ($\Omega$-cm) between about $6.0 \times 10^{13}$ and about $1.0 \times 10^{14}$. Methods of making and/or assembling such intravascular devices/systems are also provided.

15 Claims, 8 Drawing Sheets

(51) Int. Cl.
*A61M 25/09* (2006.01)
*A61B 5/0215* (2006.01)
*A61B 5/06* (2006.01)
*A61M 25/00* (2006.01)
*A61B 1/00* (2006.01)

(52) U.S. Cl.
CPC ......... *A61B 1/0011* (2013.01); *A61B 1/00114* (2013.01); *A61B 5/064* (2013.01); *A61M 2025/0002* (2013.01); *A61M 2025/09108* (2013.01); *A61M 2025/09183* (2013.01); *Y10T 29/49117* (2015.01)

(56) References Cited

U.S. PATENT DOCUMENTS

| | | | |
|---|---|---|---|
| 6,471,656 | B1 | 10/2002 | Shalman et al. |
| 7,967,762 | B2 | 6/2011 | Corl et al. |
| 9,351,687 | B2 | 5/2016 | Burkett |
| 2003/0191400 | A1 | 10/2003 | Shalman et al. |
| 2006/0241505 | A1 | 10/2006 | Ahmed et al. |
| 2007/0028698 | A1* | 2/2007 | Guziak ................ A61B 5/0215 73/729.2 |
| 2008/0101532 | A1 | 5/2008 | Tkaczyk et al. |
| 2008/0228086 | A1 | 9/2008 | Johnson et al. |
| 2009/0088650 | A1* | 4/2009 | Corl .................... A61B 5/0215 600/486 |
| 2010/0234698 | A1 | 9/2010 | Manstrom et al. |
| 2010/0280396 | A1 | 11/2010 | Zhang |
| 2011/0071404 | A1 | 3/2011 | Schmitt et al. |
| 2011/0251497 | A1* | 10/2011 | Corl .................... A61B 5/0215 600/488 |
| 2012/0065623 | A1 | 3/2012 | Nelson, III et al. |
| 2012/0093266 | A1 | 4/2012 | Sun et al. |
| 2014/0066791 | A1 | 3/2014 | Burkett |

OTHER PUBLICATIONS

"Material Properties", BASF, http://wwwstage.basf.com/urethanechemicals/pdfs/tpu/mechanprop.pdf, retrieved Nov. 18, 2016.*
Loctite® 5248™ Technical Data Sheet, Oct. 2004.*
NuSil MED-4930 Technical Data Sheet, May 2014.*
European Patent Office, "European Search Report" for Application No. 12825326.7, (PCT/US2012051566), dated Mar. 16, 2015, 7 pages.
European Patent Office, "European Search Report" for Application No. 12825326.7, (PCT/US2012051570), dated Mar. 16, 2015, 8 pages.
International Search Report and Written Opinion received in Patent Cooperation Treaty Application No. PCT/US2013/057647, dated Dec. 12, 2013, 11 pages.
Russian Patent Office, "Office Action" for Application No. 2014110701, dated May 4, 2016, 17 pages with English translation.
Russian Patent Office, "Office Action" for Application No. 2014110702, dated May 4, 2016, 14 pages with English translation.
Loctite® 5248™ Technical Data Sheet Oct. 2004, 3 pages.
Dymax® 1128A-M Series Product Data Sheet dated Mar. 6, 2012, 3 pages.
European Patent Office, "Extended European Search Report" for Application No. 16188188.3, dated Jan. 3, 2017, 10 pages.
Mynard JP et al: "Accurate Automatic Detection of End-Diastole From Left Ventricular Pressure Using Peak Curvature", IEEE Transactions on Biomedical Engineering, Nov. 1, 2008, 7 pages.

* cited by examiner

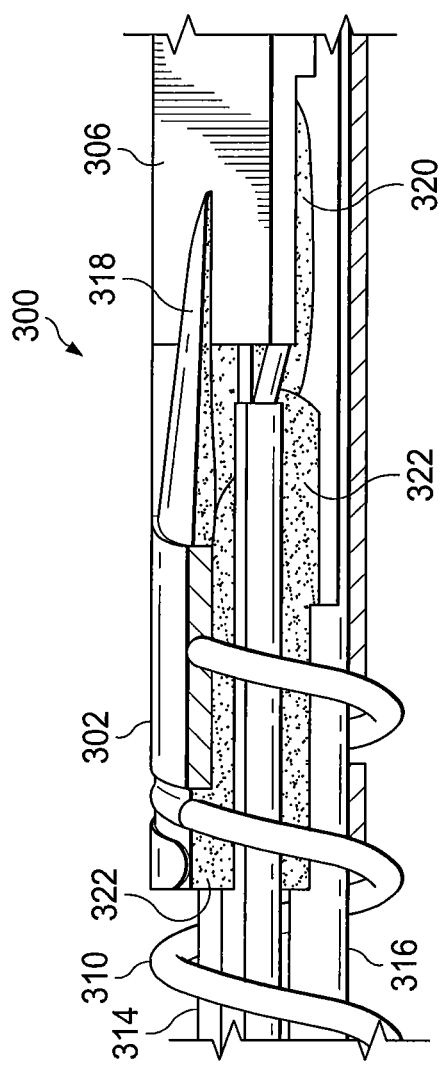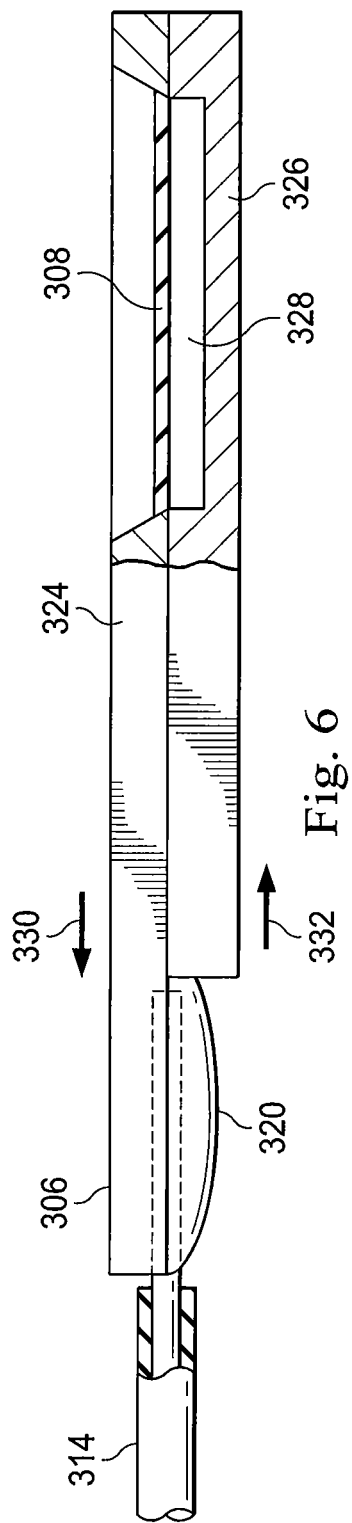
Fig. 5
Fig. 6

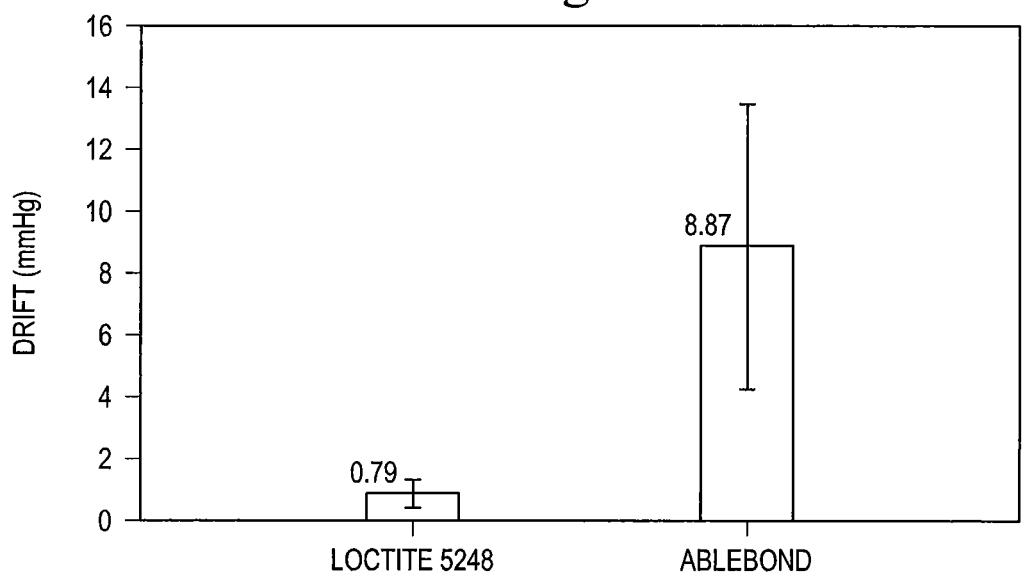

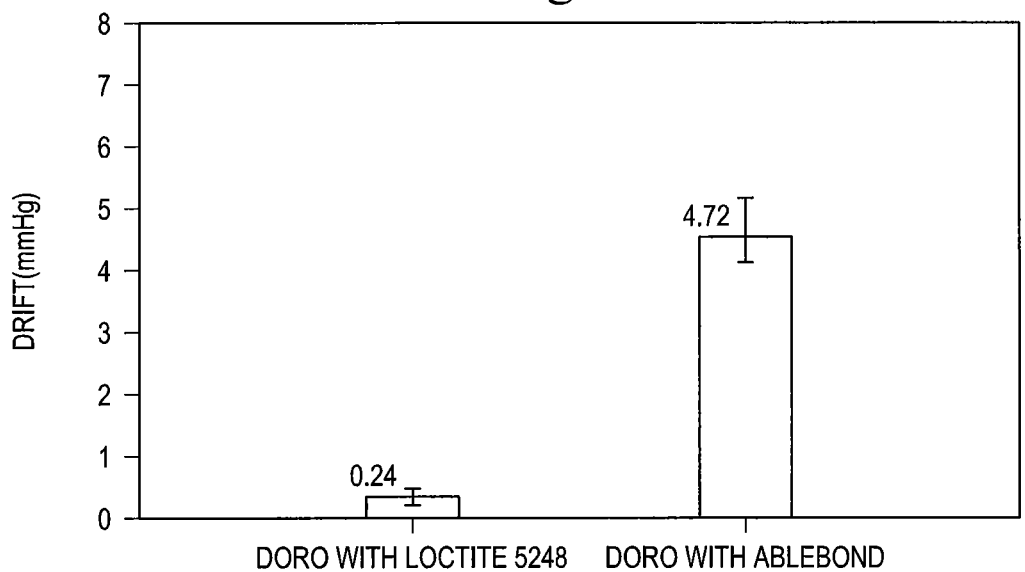
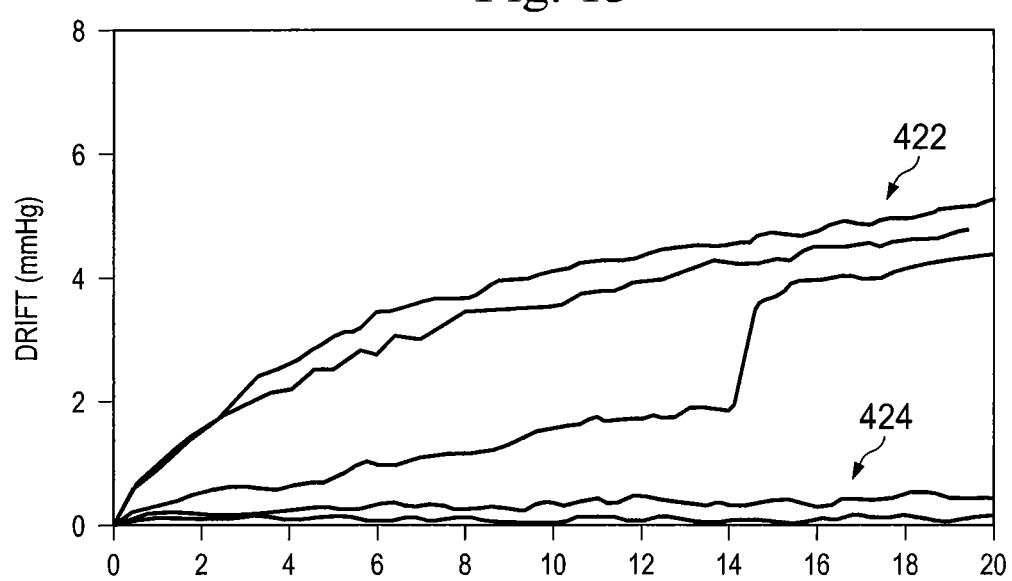

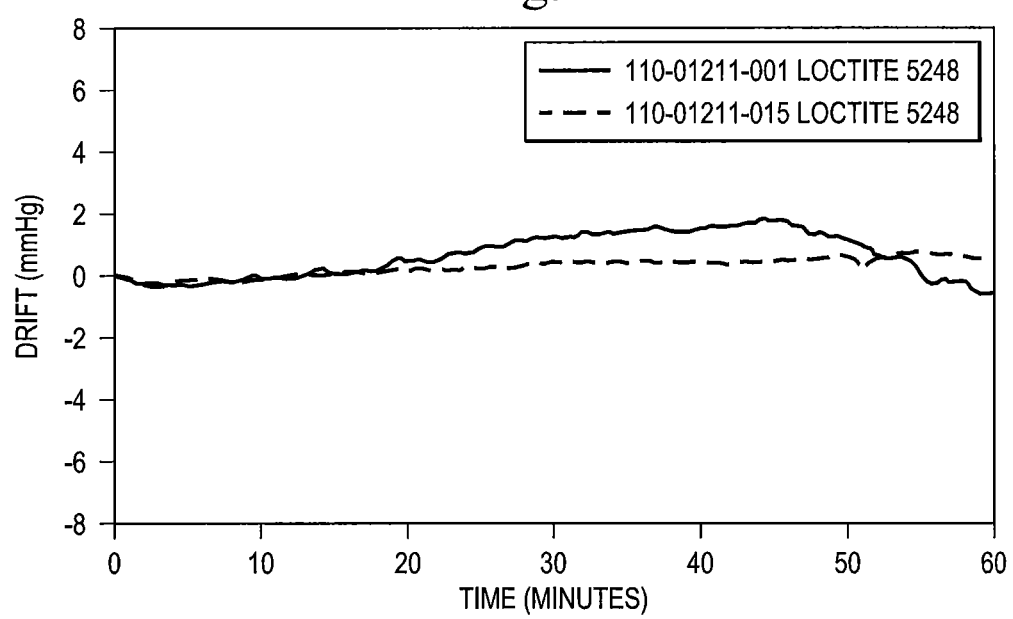

PRESSURE SENSING INTRAVASCULAR DEVICES WITH REDUCED DRIFT AND ASSOCIATED SYSTEMS AND METHODS

CROSS-REFERENCE TO RELATED APPLICATIONS

The present application claims priority to and the benefit of U.S. Provisional Patent Application No. 61/695,955, filed Aug. 31, 2012, which is hereby incorporated by reference in its entirety.

TECHNICAL FIELD

The present disclosure relates to intravascular devices, systems, and methods. In some embodiments, the intravascular devices are pressure sensing guidewires.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Intravascular catheters and guide wires are utilized to measure the pressure within the blood vessel. To date, guidewires containing pressure sensors have suffered from reduced handling characteristics compared to standard guidewires that do not contain such components. Further, pressure-sensing guide wires have also suffered from reduced precision and accuracy characteristics with respect to making intravascular pressure measurements when compared to larger pressure-sensing devices, such as aortic pressure-sensing catheters. In particular, to date pressure-sensing guide wires have suffered from drift. Drift causes the pressure reading provided by the pressure-sensing guide wire to change (i.e., increase or decrease) over time as a result of factors associated with the device itself unrelated to the actual pressure within the vessel. As a result, in order to ensure proper FFR calculations, pressure-sensing guide wire must be repeatedly normalized (i.e., relative to an aortic pressure measurement made by a pressure-sensing catheter) during a procedure. This can increase the amount of time necessary to perform the procedure, require administration of additional pharmaceuticals (e.g., adenosine) to the patient, or both, which increases the chances for unwanted complications during the procedure.

Accordingly, there remains a need for improved intravascular devices, systems, and methods that include one or more pressure sensing components with no or minimal drift within a guide wire.

SUMMARY

Embodiments of the present disclosure are directed to intravascular devices, systems, and methods.

In some embodiments, a method of assembling a guidewire is provided. The method includes providing a sensor housing having an outer diameter of 0.018" or less, the sensor housing having an inner cavity sized and shaped for receiving a pressure sensor, the inner cavity defined by an inner wall of the sensor housing; positioning a pressure sensor within the inner cavity of the housing; electrically coupling a plurality of conductors to the pressure sensor such that the electrical connections between the plurality of conductors and the pressure sensor are within the inner cavity of the housing; and introducing a potting material into the inner cavity such that the potting material covers the electrical connections, wherein the potting material has a durometer hardness between about 20 Shore A and about 50 Shore A.

In some instances, the introduced potting material has a durometer hardness of approximately 25-30 Shore A, a moisture absorption rate of about 0% per twenty-four hours, a linear shrinkage of 0%, a coefficient of thermal expansion (m/m/-° C.) of between about $1.0 \times 10^{-5}$ and about $5.0 \times 10^{-4}$, and/or a volume resistivity ($\Omega$-cm) between about $6.0 \times 10^{13}$ and about $1.0 \times 10^{14}$. Further, the introduced potting material is a UV-cured potting material with a secondary humidity cure or a secondary heat cure in some implementations. Accordingly, in some instances the method also includes curing the potting material with a UV source. Further, in some implementations electrically coupling the plurality of conductors to the pressure sensor comprises soldering. The method also includes coupling the sensor housing to a distal portion of a flexible elongate member having an outer diameter of 0.018" or less in some instances. In some embodiments, the method also includes positioning the plurality of conductors within a lumen of the flexible elongate member such that the plurality of conductors extend through the lumen from the distal portion of the flexible elongate member to a proximal portion of the flexible elongate member. Coupling the sensor housing to the distal portion of the flexible elongate member includes coupling a proximal portion of the sensor housing to a first flexible element positioned between the distal portion of the flexible elongate member and the proximal portion of the sensor housing in some instances. The method also includes coupling a distal portion of the sensor housing to a second flexible element in some implementations. In that regard, in some instances at least one of the first and second flexible elements comprises a coil or a polymer tubing.

In some embodiments, a guide wire is provided. The guide wire includes a flexible elongate body having a proximal portion, a distal portion, and a lumen extending along a length of the flexible elongate body between the proximal and distal portions; a pressure sensor coupled to the distal portion of the flexible elongate body; a plurality of conductors electrically coupled to the pressure sensor and extending through the lumen of the flexible elongate body to the proximal portion of the flexible elongate body; and a potting material covering electrical connections between the plurality of conductors and the pressure sensor, wherein the potting material has a durometer hardness between about 20 Shore A and about 50 Shore A. In some instances, the potting material has a durometer hardness of approximately 25-30 Shore A, a moisture absorption rate of about 0% per twenty-four hours, a linear shrinkage of 0%, a coefficient of thermal expansion (m/m/-° C.) of between about $1.0 \times 10^{-5}$ and about $5.0 \times 10^{-4}$, and/or a volume resistivity (Ω-cm) between about $6.0 \times 10^{13}$ and about $1.0 \times 10^{14}$. Further, the potting material is a UV-cured potting material with a secondary humidity cure or a secondary heat cure in some implementations.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 5 is a diagrammatic cross-sectional, close up perspective view of the section of the distal portion of the intravascular device of FIGS. 3 and 4.

FIG. 6 is a diagrammatic cross-sectional, side view of inner components of the distal portion of the intravascular device of FIG. 3 according to an embodiment of the present disclosure.

FIG. 9 is a graph illustrating absolute 1-hour drift characteristics of an intravascular device using a potting material according to an embodiment of the present disclosure compared to absolute 1-hour drift characteristics of an intravascular device using an alternative potting material.

FIG. 10 is a graph illustrating absolute initial offset characteristics of an intravascular device using a potting material according to an embodiment of the present disclosure compared to absolute initial offset characteristics of an intravascular device using an alternative potting material.

FIG. 12 is a graph illustrating a maximum drift of an intravascular device using a potting material according to an embodiment of the present disclosure compared to a maximum drift of an intravascular device using an alternative potting material in a twenty minute animal study.

FIG. 13 is a graph illustrating drift characteristics of intravascular devices using a potting material according to an embodiment of the present disclosure compared to drift characteristics of intravascular devices using an alternative potting material in a twenty minute animal study.

FIG. 14 is a graph illustrating drift characteristics of intravascular devices using a potting material according to an embodiment of the present disclosure in a one hour animal study.

DETAILED DESCRIPTION

Figure 1:
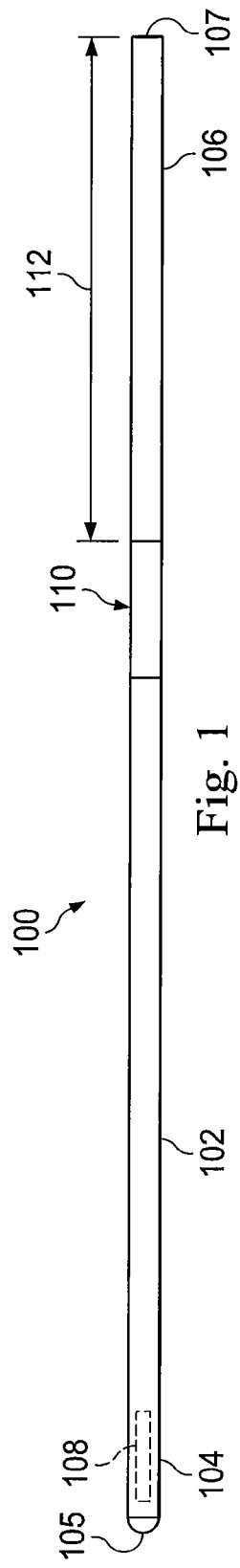
FIG. 1 is a diagrammatic, schematic side view of an intravascular device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guidewires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include at least one pressure sensing component, which may be an electronic, optical, or electro-optical component. Further, in some implementations the flexible elongate members of the present disclosure include an electronic, optical, or electro-optical component in addition to the pressure sensing component. For example, without limitation, a flexible elongate member may include one or more of the following types of components: a pressure sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are configured to communicate the data to an external device for processing and/or display.

The pressure sensing component(s) and/or other electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The pressure sensing component(s) and/or other electronic, optical, and/or electro-optical components and the associated communication lines are sized and shaped to allow for the diameter of the flexible elongate member to be very small. For example, the outside diameter of the elongate member, such as a guidewire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm)). As such, the flexible elongate members incorporating the pressure sensing component(s) and/or other electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens. Accordingly, in some instances the devices and systems of the present disclosure have applications related to organs including the liver, heart, kidneys, gall bladder, pancreas, lungs; ducts; intestines; nervous system structures including the brain, dural sac, spinal cord and peripheral nerves; the urinary tract; as well as valves within the blood or other systems of the body.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal end 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Further, in some embodiments the connector 110 provides both electrical and optical connections to both electrical conductor(s) and optical communication pathway(s) coupled to the component 108. In that regard, it should again be noted that component 108 is comprised of a plurality of elements in some instances. In some instances, the connector 110 is configured to provide a physical connection to another device, either directly or indirectly. In other instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. Generally, any number of electrical conductors, optical pathways, and/or combinations thereof can extend along the length of the flexible elongate member 102 between the connector 110 and the component 108. In some instances, between one and ten electrical conductors and/or optical pathways extend along the length of the flexible elongate member 102 between the connector 110 and the component 108. For the sake of clarity and simplicity, the embodiments of the present disclosure described below include three electrical conductors. However, it is understood that the total number of communication pathways and/or the number of electrical conductors and/or optical pathways is different in other embodiments. More specifically, the number of communication pathways and the number of electrical conductors and optical pathways extending along the length of the flexible elongate member 102 is determined by the desired functionality of the component 108 and the corresponding elements that define component 108 to provide such functionality.

Figure 2:
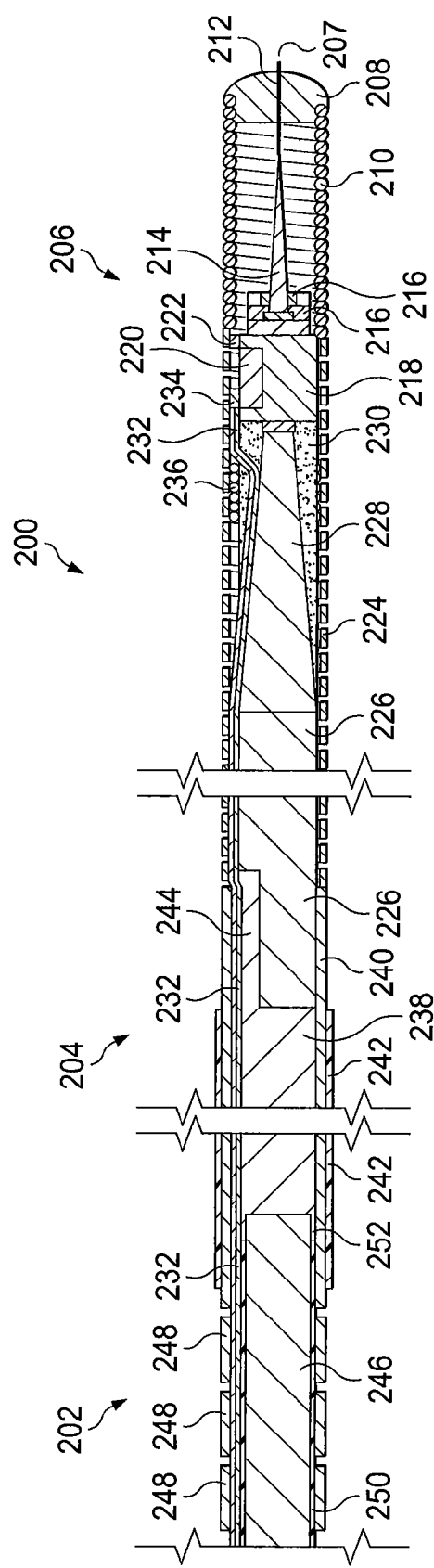
FIG. 2 is diagrammatic cross-sectional side view of an intravascular device according to an embodiment of the present disclosure.

Referring now to FIG. 2, shown therein is a cross-sectional side view of an intravascular device 200 according to an embodiment of the present disclosure. In that regard, the intravascular device 200 is provided as an exemplary embodiment of the type of intravascular device into which the potting materials, including the associated methods and structural arrangements, described below with respect to FIGS. 3-14 can be implemented. However, it is understood that no limitation is intended thereby and that the concepts of the present disclosure are applicable to a wide variety of intravascular devices, including those described in U.S. Pat. No. 7,967,762 and U.S. Patent Application Publication No. 2009/0088650, each of which is hereby incorporated by reference in its entirety.

As shown in FIG. 2, the intravascular device 200 includes a proximal portion 202, a middle portion 204, and a distal portion 206. Generally, the proximal portion 202 is configured to be positioned outside of a patient, while the distal portion 206 and a majority of the middle portion 204 are configured to be inserted into the patient, including within human vasculature. In that regard, the middle and distal portion 204 have an outer diameter between about 0.0007" (0.0178 mm) and about 0.118" (3.0 mm) in some embodiments, with some particular embodiments having an outer diameter of approximately 0.014" (0.3556 mm) or approximately 0.018" (0.4572 mm)). In the illustrated embodiment of FIG. 2, the intravascular device 200 has an outer diameter of 0.014" (0.3556 mm).

As shown, the distal portion 206 of the intravascular device 200 has a distal tip 207 defined by an element 208. In the illustrated embodiment, the distal tip 207 has a rounded profile. In some instances, the element 208 is radiopaque such that the distal tip 207 is identifiable under x-ray, fluoroscopy, and/or other imaging modalities when positioned within a patient. In some particular instances, the element 208 is solder secured to a flexible element 210 and/or a flattened tip core 212. In that regard, in some instances the flexible element 210 is a coil spring. The flattened tip core 212 extends distally from a distal portion of a core 214. As shown, the distal core 214 tapers to a narrow profile as it extends distally towards the distal tip 207. In some instances, the distal core 214 is formed of a stainless steel that has been ground down to have the desired tapered profile. In some particular instances, the distal core 214 is formed of high tensile strength 304V stainless steel. In an alternative embodiment, the distal core 214 is formed by wrapping a stainless steel shaping ribbon around a Nitinol core and/or extending a stainless steel shaping ribbon alongside (e.g., parallel to) a Nitinol core. In some embodiments, the distal core 214 is secured to a mounting structure 218 by mechanical interface, solder, adhesive, combinations thereof, and/or other suitable techniques as indicted by reference numerals 216. The mounting structure 218 is configured to receive and securely hold a component 220. In that regard, the component 220 is one or more of an electronic component, an optical component, and/or electro-optical component. For example, without limitation, the component 220 may be one or more of the following types of components: a pressure sensor, a temperature sensor, an imaging element, an optical fiber, an ultrasound transducer, a reflector, a mirror, a prism, an ablation element, an RF electrode, a conductor, and/or combinations thereof.

The mounting structure 218 is fixedly secured within the distal portion 206 of the intravascular device 200. The mounting structure 218 may be fixedly secured to a core wire (i.e., a single core running along the length of the mounting structure), flexible elements or other components surrounding at least a portion of the mounting structure (e.g., coils, polymer tubing, etc.), and/or other structure(s) of the intravascular device positioned adjacent to the mounting structure. In the illustrated embodiment, the mounting structure is disposed at least partially within flexible element 210 and/or a flexible element 224 and secured in place by an adhesive or solder 222. In some instances, the flexible elements 210 and 224 are flexible coils. In one particular embodiment, the flexible element 224 is ribbon coil covered with a polymer coating. For example, in one embodiment the flexible element 224 is a stainless steel ribbon wire coil coated with polyethylene terephthalate (PET). In some implementations, flexible element 224 acts as a substrate for lubricious coating. In that regard, a hydrophilic is utilized in some instances. In another embodiment, the flexible element is a polyimide tubing that has a ribbon wire coil embedded therein. An adhesive is utilized to secure the mounting structure 218 to the flexible element 210 and/or the flexible element 224 in some implementations. Accordingly, in some instances the adhesive is urethane acrylate, cyanoacrylate, silicone, epoxy, and/or combinations thereof.

In some embodiments, the mounting structure 218 is a housing (See, for example, device 300 of FIGS. 3-6 described below) configured to receive component 220. In some embodiments, the housing is a generally cylindrical housing having an inner opening or passage for receiving component 220. In that regard, the housing separates the flexible elements 210 and 224 from one another in some embodiments. Accordingly, in some instances the flexible element 210 is secured to a distal portion of the housing, while the flexible element 224 is secured to a proximal portion of the housing. Further still, in some embodiments mounting structure 218 is implemented as described in U.S. Provisional Patent Application No. 61/695,970 titled "MOUNTING STRUCTURES FOR COMPONENTS OF INTRAVASCULAR DEVICES" and filed on Aug. 31, 2012, now published as U.S. Patent Application Publication. No. 2014/0066791 A1, which is hereby incorporated by reference in its entirety. Further still, in some embodiments the mounting structure 218 is received within a housing. Accordingly, it is understood that the application of potting materials in the manner described below can be utilized in embodiments of intravascular devices that include a housing separate from the flexible element(s) and mounting structure, as well as embodiments that do not include a housing separate from the flexible element(s) and mounting structure.

As shown in FIG. 2, the mounting structure 218 is secured to a core 226 that extends proximally from the mounting structure towards the middle portion 204 of the intravascular device 200. In that regard, core 226 and distal core 214 are integrally formed in some embodiments such that a continuous core passes through the mounting structure. In other embodiments, core 226 and distal core 214 are separate elements. In the illustrated embodiment, a portion 228 of the core 226 tapers as it extends distally towards mounting structure 218. However, in other embodiments the core 226 has a substantially constant profile along its length. In some implementations, the diameter or outer profile (for non-circular cross-sectional profiles) of core 226 and core 214 are the same. In some implementations, a hypotube is utilized in place of core 226. Like distal core 214, the core 226 is fixedly secured to the mounting structure 218. In some instances, solder and/or adhesive is used to secure the core 226 to the mounting structure 218. In the illustrated embodiment, solder/adhesive 230 surrounds at least a part of the portion 228 of the core 226. In some instances, the solder/adhesive 230 is the solder/adhesive 222 used to secure the mounting structure 218 to the flexible element 210 and/or flexible element 224. In other instances, solder/adhesive 230 is a different type of solder or adhesive than solder/adhesive 222. In one particular embodiment, adhesive or solder 222 is particularly suited to secure the mounting structure 218 to flexible element 210, while solder/adhesive 230 is particularly suited to secure the mounting structure to flexible element 224.

A communication cable 232 extends along the length of the intravascular device 200 from the proximal portion 202 to the distal portion 206. In that regard, the distal end of the communication cable 232 is coupled to the component 220 at junction 234. The type of communication cable utilized is dependent on the type of electronic, optical, and/or electro-optical components that make up the component 220. In that regard, the communication cable 232 may include one or more of an electrical conductor, an optical fiber, and/or combinations thereof. Appropriate connections are utilized at the junction 234 based on the type of communication lines included within communication cable 232. For example, electrical connections are soldered in some instances, while optical connections pass through an optical connector in some instances. In some embodiments, the communication cable 232 is a trifilar structure. Further, it is understood that all and/or portions of each of the proximal, middle, and/or distal portions 202, 204, 206 of the intravascular device 200 may have cross-sectional profiles as shown in FIGS. 2-5 of U.S. Provisional Patent Application No. 61/665,697 filed on Jun. 28, 2012, which is hereby incorporated by reference in its entirety.

As will be discussed in greater detail below, the volume of space surrounding the junction 234 wherein the communication cable 232 is coupled to the component 220 (e.g., space within a housing containing component 220, space between the mounting structure 218 and a surrounding flexible element 210, 224, and/or other space) is filled with a potting material according to some embodiments of the present disclosure. In that regard, Applicants have found that the use of potting materials having particular material characteristics around the junction 234 provide an unexpectedly significant reduction and/or elimination of drift in pressure sensing guide wires. In some instances, the potting material is applied to a soldered connection at junction 234 prior to the component 220 being installed into the housing or mounting structure 218. More specifically, in some embodiments the potting material has a durometer hardness between about 20 Shore A and about 50 Shore A, with some particular embodiments having a durometer hardness of approximately 25-30 Shore A. Further, the potting material has a moisture absorption rate of about 0% per twenty-four hours in some implementations. In some instances, the potting material is a UV-cured potting material. In that regard, in some embodiments, the UV-cured potting material includes a secondary cure, such as a humidity cure or a heat cure. Further, the potting material has a linear shrinkage of 0% in some instances. In some implementations, the potting material has a coefficient of thermal expansion (m/m/-° C.) of between about $1.0 \times 10^{-5}$ and about $5.0 \times 10^{-4}$, with some particular embodiments having a coefficient of thermal expansion (m/m/-° C.) of about $2.89 \times 10^{-4}$. In some embodiments, the potting material has a volume resistivity (Ω-cm) between about $6.0 \times 10^{13}$ and about $1.0 \times 10^{14}$, with some particular embodiments having a volume resistivity (Ω-cm) of about $8.3 \times 10^{13}$. In some implementations, the potting material is Loctite® 5248™. In that regard, additional information about Loctite® 5248™ is available in the Loctite® 5248™ Technical Data Sheet dated October 2004, which is hereby incorporated by reference in its entirety. Additional details regarding implementation of potting materials in accordance with the present disclosure will be described below with respect to FIGS. 3-14.

Further, in some embodiments, the proximal portion 202 and/or the distal portion 206 incorporate spiral ribbon tubing as disclosed in U.S. Provisional Patent Application No. 61/665,697 filed on Jun. 28, 2012. In some instances, the use of such spiral ribbon tubing allows a further increase in the available lumen space within the device. For example, in some instances use of a spiral ribbon tubing having a wall thickness between about 0.001" and about 0.002" facilitates the use of a core wire having an outer diameter of at least 0.0095" within a 0.014" outer diameter guide wire using a trifilar with circular cross-sectional conductor profiles. The size of the core wire can be further increased to at least 0.010" by using a trifilar with the flattened oblong cross-section conductor profiles. The availability to use a core wire having an increased diameter allows the use of materials having a lower modulus of elasticity than a standard stainless steel core wire (e.g., superelastic materials such as Nitinol or NiTiCo are utilized in some instances) without adversely affecting the handling performance or structural integrity of the guide wire and, in many instances, provides improvement to the handling performance of the guide wire, especially when a superelastic material with an increased core diameter (e.g., a core diameter of 0.0075" or greater) is utilized within the distal portion 206.

The distal portion 206 of the intravascular device 200 also optionally includes at least one imaging marker 236. In that regard, the imaging marker 236 is configured to be identifiable using an external imaging modality, such as x-ray, fluoroscopy, angiograph, CT scan, MRI, or otherwise, when the distal portion 206 of the intravascular device 200 is positioned within a patient. In the illustrated embodiment, the imaging marker 236 is a radiopaque coil positioned around the tapered distal portion 228 of the core 226. Visualization of the imaging marker 236 during a procedure can give the medical personnel an indication of the size of a lesion or region of interest within the patient. To that end, the imaging marker 236 can have a known length (e.g., 0.5 cm or 1.0 cm) and/or be spaced from the element 208 by a known distance (e.g., 3.0 cm) such that visualization of the imaging marker 236 and/or the element 208 along with the anatomical structure allows a user to estimate the size or length of a region of interest of the anatomical structure. It is understood that a plurality of imaging markers 236 are utilized in some instances. In that regard, in some instances the imaging markers 236 are spaced a known distance from one another to further facilitate measuring the size or length of the region of interest.

In some instances, a proximal portion of the core 226 is secured to a core 238 that extends through the middle portion 204 of the intravascular device. In that regard, the transition between the core 226 and the core 238 may occur within the distal portion 206, within the middle portion 204, and/or at the transition between the distal portion 206 and the middle portion 204. For example, in the illustrated embodiment the transition between core 226 and core 238 occurs in the vicinity of a transition between the flexible element 224 and a flexible element 240. The flexible element 240 in the illustrated embodiment is a hypotube. In some particular instances, the flexible element is a stainless steel hypotube. Further, in the illustrated embodiment a portion of the flexible element 240 is covered with a coating 242. In that regard, the coating 242 is a hydrophobic coating in some instances. In some embodiments, the coating 242 is a polytetrafluoroethylene (PTFE) coating.

The proximal portion of core 226 is fixedly secured to the distal portion of core 238. In that regard, any suitable technique for securing the cores 226, 238 to one another may be used. In some embodiments, at least one of the cores 226, 238 includes a plunge grind or other structural modification 244 that is utilized to couple the cores together. In some instances, the cores 226, 238 are soldered together. In some instances, an adhesive is utilized to secure the cores 226, 238 together. In some embodiments, combinations of structural interfaces, soldering, and/or adhesives are utilized to secure the cores 226, 238 together. In other instances, the core 226 is not fixedly secured to core 238. For example, in some instances, the core 226 and the core 246 are fixedly secured to the hypotube 240 and the core 238 is positioned between the cores 226 and 246, which maintains the position of the core 238 between cores 226 and 246.

In some embodiments, the core 238 is formed of a different material than the core 226. For example, in some instances the core 226 is formed of Nitinol and the core 238 is formed of stainless steel. In other instances, the core 238 and the core 226 are formed of the same material. In some instances the core 238 has a different profile than the core 226, such as a larger or smaller diameter and/or a non-circular cross-sectional profile. For example, in some instances the core 238 has a D-shaped cross-sectional profile. In that regard, a D-shaped cross-sectional profile has some advantages in the context of an intravascular device 200 that includes one or more electronic, optical, or electro-optical component in that it provides a natural space to run any necessary communication cables while providing increased strength than a full diameter core. In other instances, core 238 and core 226 are made of the same material and/or have the same structure profiles such that the cores 226 and 238 form a continuous, monolithic core.

In some instances, a proximal portion of the core 238 is secured to a core 246 that extends through at least a portion of the proximal portion 202 of the intravascular device 200. In that regard, the transition between the core 238 and the core 246 may occur within the proximal portion 202, within the middle portion 204, and/or at the transition between the proximal portion 202 and the middle portion 204. For example, in the illustrated embodiment the transition between core 238 and core 246 is positioned distal of a plurality of conducting bands 248. In that regard, in some instances the conductive bands 248 are portions of a hypotube. Proximal portions of the communication cable 232 are coupled to the conductive bands 248. In that regard, in some instances each of the conductive bands is associated with a corresponding communication line of the communication cable 232. For example, in embodiments where the communication cable 232 consists of a trifilar, each of the three conductive bands 248 are connected to one of the conductors of the trifilar, for example by soldering each of the conductive bands to the respective conductor. Where the communication cable 232 includes optical communication line(s), the proximal portion 202 of the intravascular device 200 includes an optical connector in addition to or instead of one or more of the conductive bands 248. An insulating layer or sleeve 250 separates the conductive bands 248 from the core 246. In some instances, the insulating layer 250 is formed of polyimide.

As noted above, the proximal portion of core 238 is fixedly secured to the distal portion of core 246. In that regard, any suitable technique for securing the cores 238, 246 to one another may be used. In some embodiments, at least one of the cores includes a structural feature that is utilized to couple the cores together. In the illustrated embodiment, the core 238 includes an extension 252 that extends around a distal portion of the core 246. In some instances, the cores 238, 246 are soldered together. In some instances, an adhesive is utilized to secure the cores 238, 246 together. In some embodiments, combinations of structural interfaces, soldering, and/or adhesives are utilized to secure the cores 238, 246 together. In other instances, the core 226 is not fixedly secured to core 238. For example, in some instances and as noted above, the core 226 and the core 246 are fixedly secured to the hypotube 240 and the core 238 is positioned between the cores 226 and 246, which maintains the position of the core 238 between cores 226 and 246. In some embodiments, the core 246 is formed of a different material than the core 238. For example, in some instances the core 246 is formed of Nitinol and/or NiTiCo (nickel-titanium-cobalt alloy) and the core 238 is formed of stainless steel. In that regard, by utilizing a Nitinol core within the conductive bands 248 instead of a stainless steel the likelihood of kinking is greatly reduced because of the increased flexibility of the Nitinol core compared to a stainless steel core. In other instances, the core 238 and the core 246 are formed of the same material. In some instances the core 238 has a different profile than the core 246, such as a larger or smaller diameter and/or a non-circular cross-sectional profile. In other instances, core 238 and core 246 are made of the same material and/or have the same structure profiles such that the cores 238 and 246 form a continuous, monolithic core.

Figure 3:
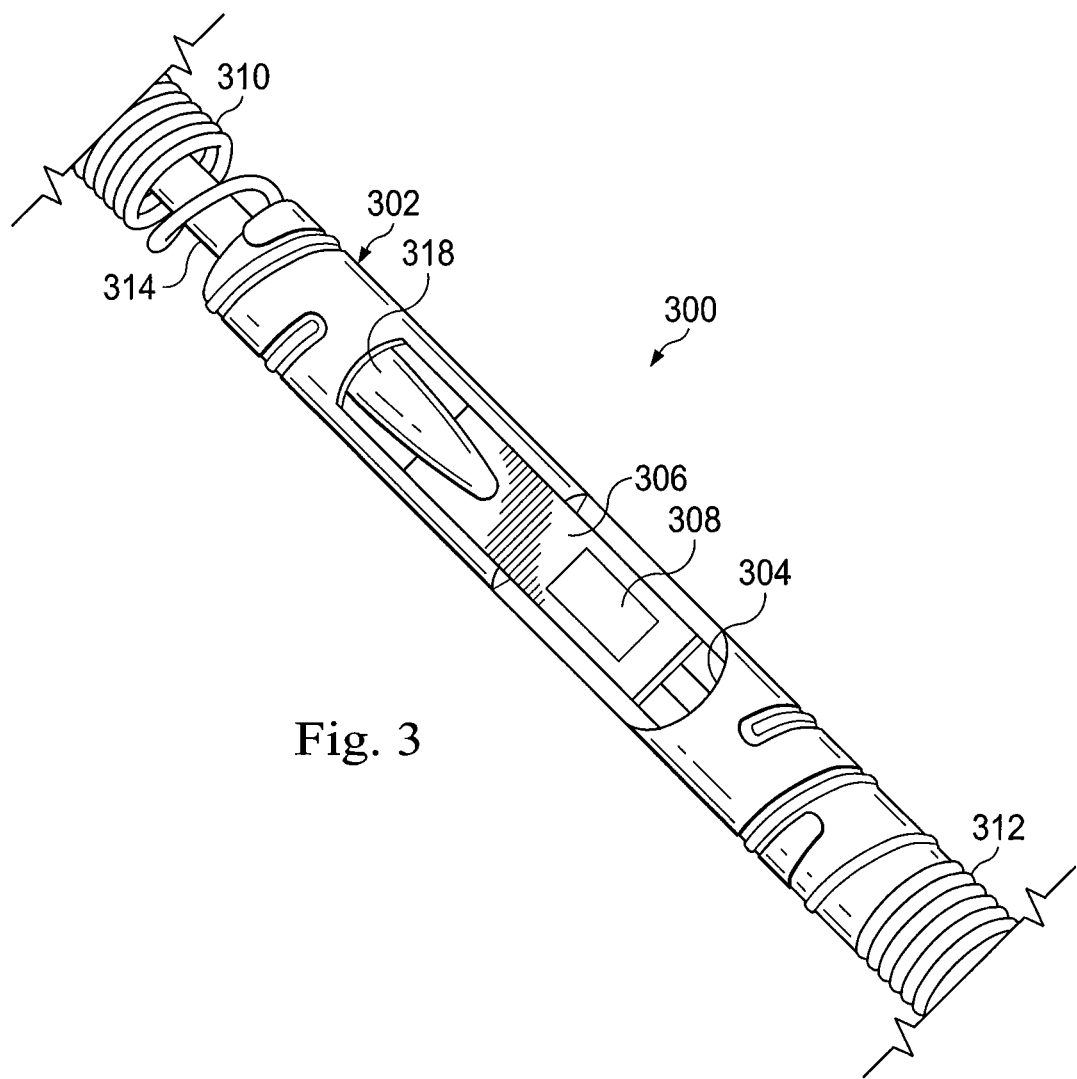
FIG. 3 is a diagrammatic perspective view of a distal portion of an intravascular device according to an embodiment of the present disclosure.

Referring now to FIGS. 3-6, shown therein are aspects of a pressure sensing intravascular device 300 incorporating potting materials according to an embodiment of the present disclosure. In that regard, FIG. 3 illustrates a section of a distal portion of the intravascular device 300. As shown, the intravascular device 300 includes a housing 302 having an opening 304 that exposes a sensing component 306 to a surrounding environment. In the illustrated embodiment, the housing 302 is generally cylindrical in shape with an outer diameter of approximately 0.014" (0.3556 mm). Further, in the illustrated embodiment the sensing component 306 is a pressure sensor having a diaphragm 308. In that regard, the diaphragm 308 is exposed to the surrounding environment or ambient by the opening 304 in the housing such that the diaphragm 308 is responsive to the pressure of the surrounding environment/ambient. In that regard, the amount of pressure imparted on the diaphragm 308 determines the resulting signal generated by the pressure sensing component 306.

Figure 4:
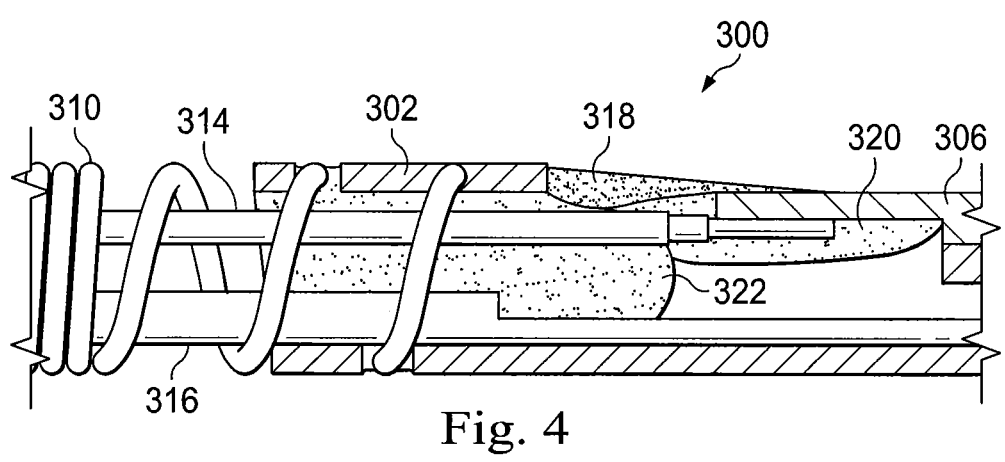
FIG. 4 is a diagrammatic cross-sectional, close up side view of a section of the distal portion of the intravascular device of FIG. 3 according to an embodiment of the present disclosure.

The housing 302 is coupled to a proximal flexible element 310 and a distal flexible element 312. In the illustrated embodiment, portions of the flexible elements 310 and 312 threaded into corresponding openings or recesses formed in the housing 302. However, the flexible elements 310 and 312 may be connected to the housing any suitable technique. As shown, a communication cable 314 consisting of three conductors extends proximally from the pressure sensing component 306. Also, as best seen in FIGS. 4 and 5, a core 316 extends proximally from the pressure sensing component 306. In some instances, the core 316 also extends distally from the pressure sensing component 306. In some embodiments, a portion of the core 316 configured to interface with the pressure sensing component 306 and/or an associated mounting structure has a reduced profile relative to adjacent portions of the core. The conductors of the communications cable 314 are electrically coupled to the pressure sensing component 306. In that regard, in some instances distal portions of each of the three conductors are exposed (e.g., by removing any surrounding insulating layer(s)) and soldered (or otherwise electrically coupled) to an electrical connector of the pressure sensing component.

With the communications cable 314 electrically coupled to the pressure sensing component 306 a potting material 320 is introduced over the connections between the communication cable 314 and the pressure sensing component 306. In that regard, in some instances at least some or all of the potting material 320 is positioned over the connections between the communication cable 314 and the pressure sensing component 306 prior to positioning those components within the housing 302. In that regard, application of the potting material 320 prior to positioning within the housing 302 facilitates modular assembly, where the communication cable 314 and pressure sensing component 306 can be preassembled and tested as a modular component before being positioned within the housing 302. This can speed up manufacturing and increase yields in some instances. In other instances, however, the potting material 320 is introduced after the pressure sensing component 306 and communication cable 314 are positioned within the housing 302.

The potting material 320 completely covers all exposed wire, solder, and pad contacts on the pressure sensing component 306. In that regard, in some manufacturing implementations an operator or corresponding machine applies the potting material 320 onto the trifilar insulation. In some instances, the pressure sensing component 306 has a split design such that the pads are on a surface that is approximately at the mid thickness of the sensor and the adhesive is applied to go up to a thicker section of the pressure sensing component. Further, the volume of potting material applied is controlled via an EFD dispenser in some instances, which provides control over the resulting thickness of the potting material 320. Based on the specific design parameters of the connection between the communication cable 314 and the pressure sensing component, minimum and maximum volume limits can be set to define a range of volumes that provide adequate coverage. In that regard, because the potting material 320 is applied at the sensor subassembly level in some instances, it can be important that the thickness not be too large such that the resulting bulge of potting material may push against other components (e.g., the core wire) once installed into the housing 302. In some implementations, the potting material 320 has a thickness such that it extends only between about 0.0020" to 0.0030" above the solder joints between the communication cable 314 and the pressure sensing component 306. However, larger and smaller thicknesses are utilized in other implementations. When applied at the subassembly level, the potting material 320 contacts the communication cable 314 (insulation and conductive wire), solder, sensor pads, pressure sensing component 306 (silicon and glass portions in some instances). In that regard, in some embodiments the pressure sensing component 306 implements one or more features of the pressure sensors disclosed in U.S. Pat. No. 7,967,762, which is hereby incorporated by reference in its entirety, including the types of materials and geometrical arrangements. When applied as part of the housing assembly, the potting material 320 further contacts one or more of the core, sensor housing 302, solder, and other adhesives or potting materials used in the assembly process.

Applicants have found that the use of potting materials having particular material characteristics over the connections between the communication cable 314 and the pressure sensing component 306 provide an unexpectedly significant reduction and/or elimination of drift in pressure sensing intravascular device 300. To that end, the unexpected results associated with the particular potting materials of the present disclosure are discussed below with respect to FIGS. 7-14. In that regard, in some embodiments the potting material 320 has a durometer hardness between about 20 Shore A and about 50 Shore A, with some particular embodiments having a durometer hardness of approximately 25-30 Shore A. Further, the potting material 320 has a moisture absorption rate of about 0% per twenty-four hours in some implementations. In some instances, the potting material 320 is a UV-cured potting material. The curing time is dependent upon the UV intensity output. In some instances, the UV output is optimized for a curing time between about 5 seconds and about 60 seconds, with some particular embodiments having a curing time between about 15 seconds and about 30 seconds. In that regard, in some embodiments, the UV-cured potting material includes a secondary cure, such as a humidity cure or a heat cure. Further, the potting material 320 has a linear shrinkage of 0% in some instances. In some implementations, the potting material 320 has a coefficient of thermal expansion (m/m/-° C.) of between about $1.0 \times 10^{-5}$ and about $5.0 \times 10^{-4}$, with some particular embodiments having a coefficient of thermal expansion (m/m/-° C.) of about $2.89 \times 10^{-4}$. In some embodiments, the potting material 320 has a volume resistivity (Ω-cm) between about $6.0 \times 10^{13}$ and about $1.0 \times 10^{14}$, with some particular embodiments having a volume resistivity (Ω-cm) of about $8.3 \times 10^{13}$. In some implementations, the potting material 320 is Loctite® 5248™. In that regard, additional information about Loctite® 5248™ is available in the Loctite® 5248™ Technical Data Sheet dated October 2004, which is hereby incorporated by reference in its entirety. In other instances, the adhesive 320 is selected from the group of adhesives consisting of Loctite 5031-34 Shore A, Loctite 5040-30 Shore A, Loctite 5091-34 Shore A, Loctite 5240-45 Shore A, and/or other suitable adhesives.

Then, with the potting material applied to the soldered electrical connection and the pressure sensing component 306 positioned within the housing 302, some of the spaces within the housing around the pressure sensing component 306, communications cable 314, core 316, and/or other elements are filled with a potting material, adhesive, and/or covered with an encapsulant. For example, in the illustrated embodiment, an adhesive 318 is introduced between the housing 302 and the body of the pressure sensing component 306 adjacent to the opening 304. In some embodiments, the adhesive 318 is Dymax® Multi-Cure® 1128A-M Series Gel Adhesive. In that regard, additional information about Dymax® Multi-Cure® 1128A-M Series Gel Adhesive is available in the Dymax® 1128A-M Series Product Data Sheet dated Mar. 6, 2012, which is hereby incorporated by reference in its entirety. In other instances, the adhesive 318 is selected from the group of adhesives consisting of Loctite 5031-34 Shore A, Loctite 5040-30 Shore A, Loctite 5091-34 Shore A, Loctite 5240-45 Shore A, Loctite 5248-25 Shore A, Loctite 3211-51 Shore D, and/or other suitable adhesives.

Further, as shown, an adhesive 322 is introduced within the proximal portion of the housing 302, within a distal portion of the flexible element 310, and around the communication cable 314 and core 316 proximal of the pressure sensing component 306 to secure flexible element 310 to the housing 302. Generally, the adhesive 322 fills any gaps in the proximal portion of the housing 302 between the components positioned therein. In some embodiments, the adhesive 322 is Dymax® Multi-Cure® 1128A-M Series Adhesive. In that regard, additional information about Dymax® Multi-Cure® 1128A-M Series Adhesive is available in the Dymax® 1128A-M Series Product Data Sheet dated Mar. 6, 2012, which is hereby incorporated by reference in its entirety. A gel version of the Dymax® 1128 adhesive is used in some instances because it can be applied to a specific area and won't thin out prior to curing. Further, a low viscosity material is applied in some instances because it will wick into all of the threads of a coil (e.g., when flexible element 310 is implemented as a coil) and into the proximal end of the housing. In some instances, the adhesive 322 is Loctite 4311-51 Shore D or other suitable adhesive.

Referring more particularly to FIG. 6, shown therein are additional details regarding the structural arrangement of the pressure sensing component 306 and the interaction with potting material 320 according to an embodiment of the present disclosure. As shown, in the illustrated embodiment the pressure sensing component 306 includes a layer 324 that is coupled to a layer 326. In that regard, in some instances layers 324 and 326 are formed of different materials. For example, in some implementations layer 324 is formed of silicon or other suitable semiconductor substrate, while layer 326 is formed of glass. As shown, a cavity or recess 328 formed in layer 326 is covered by the diaphragm 308. Accordingly, in some instances the recess 328 acts as a reference pressure chamber for the diaphragm 308. As also shown, the potting material 320 covers the electrical coupling between the exposed conductors of the communication cable 314 and the electrical pads of the pressure sensing component 306. In that regard, the potting material 320 adheres to and/or abuts to portions of layer 324 and layer 326. As a result, expansion of the traditional potting materials having an increased hardness relative to those of the present disclosure can impart forces on layers 324 and 326 that result in undesirable variance or drift in the pressure readings of the pressure sensing component 306. For example, in some instances the expansion of traditional potting materials impart a shear stress between the layers 324 and 326 as indicated by arrows 330 and 332, which represent a directional force imparted on the layers respectively. The potting materials 320 of the present disclosure substantially reduce and/or eliminate the forces applied to the layers 324 and 326 by having no linear shrinkage, lower thermal expansion, and lower durometer hardness compared to traditional potting materials.

Figure 7:
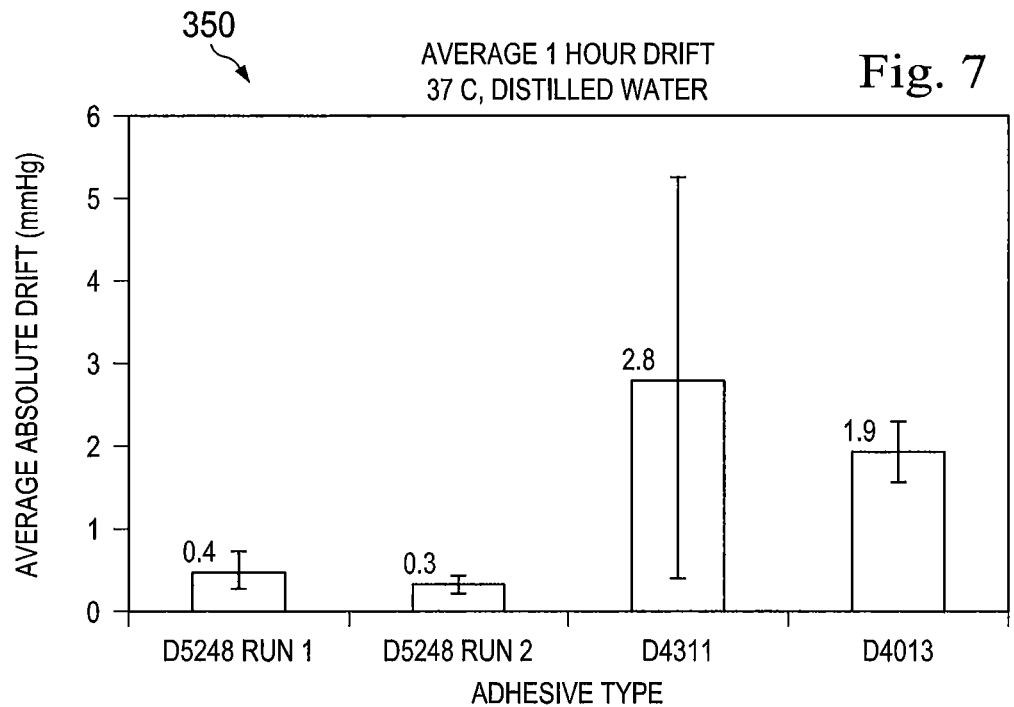
FIG. 7 is a graph illustrating average drift characteristics of an intravascular device using a potting material according to an embodiment of the present disclosure compared to average drift characteristics of an intravascular devices using alternative potting materials in distilled water.

Referring now to FIGS. 7-14, shown therein are various graphs illustrating the extreme benefits of the embodiments of the present disclosure in terms of reducing and/or eliminating drift in pressure-sensing guide wires. Referring initially to FIG. 7, shown therein is a graph 350 illustrating average drift characteristics of an intravascular device using a potting material according to an embodiment of the present disclosure compared to average drift characteristics of an intravascular devices using alternative potting materials in distilled water. The two bars on the left side of the graph 350 illustrate the average absolute drift (mmHg) over one hour in distilled water at a temperature of 37° C. for the intravascular device using a potting material according to an embodiment of the present disclosure, in particular Loctite® 5248™, while the two bars on the right side of the graph illustrate the average absolute drift (mmHg) over one hour in distilled water at a temperature of 37° C. for the intravascular device using alternative potting materials, in particular Loctite® 4311™ and Loctite® 4013™. As shown, the average absolute drift (mmHg) for the intravascular device using a potting material according to an embodiment of the present disclosure is significantly less than the alternative potting materials. In particular, the alternative potting materials result in a drift five to nine times as large as the potting materials of the present disclosure, with the two runs of Loctite® 5248™ have average drifts of 0.4 mmHg and 0.3 mmHg compared to 2.8 mmHg for Loctite® 4311™ and 1.9 mmHg for Loctite® 4013™.

Figure 8:
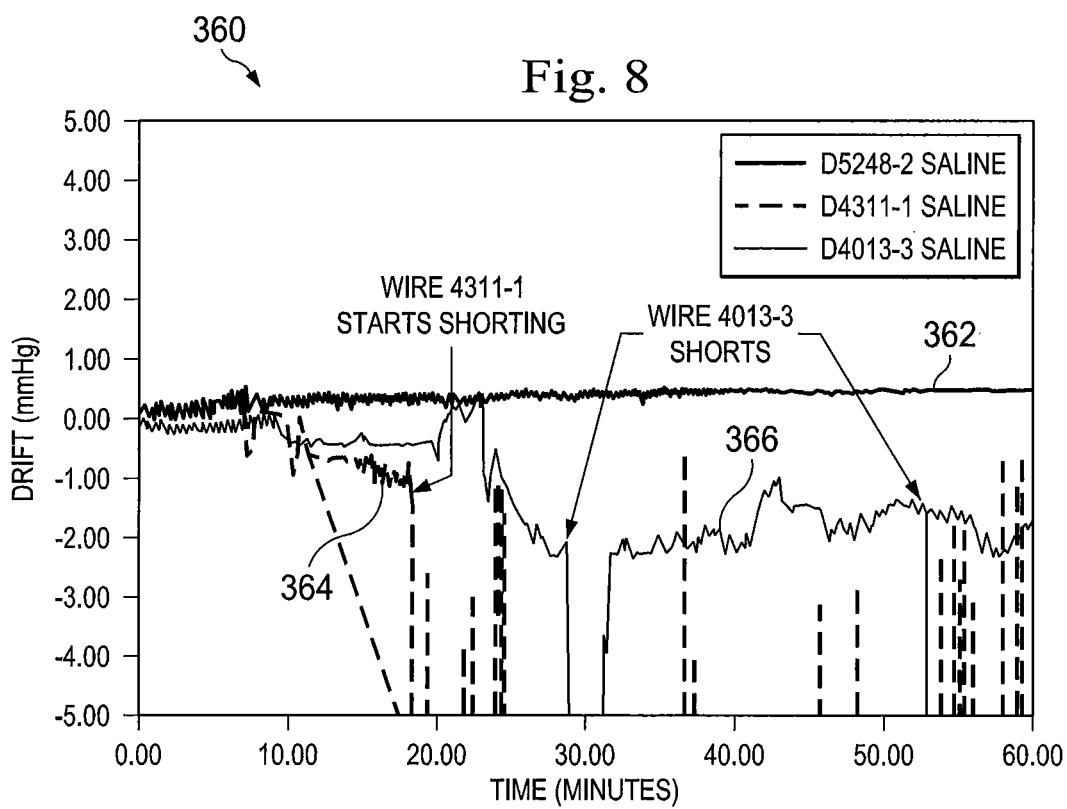
FIG. 8 is a graph illustrating drift characteristics of an intravascular device using a potting material according to an embodiment of the present disclosure compared to drift characteristics of intravascular devices using alternative potting materials in saline.

Referring now to FIG. 8, shown therein is a graph 360 illustrating drift characteristics of an intravascular device using a potting material according to an embodiment of the present disclosure compared to drift characteristics of intravascular devices using alternative potting materials in saline. In that regard, line graph 362 illustrates the drift (mmHg) over time in saline at a temperature of 37° C. for the intravascular device using a potting material according to an embodiment of the present disclosure, in particular Loctite® 5248™. Line graph 364 illustrates the drift (mmHg) over time in saline at a temperature of 37° C. for the intravascular device using an alternative potting material, in particular Loctite® 4311™. Finally, line graph 366 illustrates the drift (mmHg) over time in saline at a temperature of 37° C. for the intravascular device using another alternative potting material, in particular Loctite® 4013™. As shown, whereas the line graphs 364 and 366 associated with the alternative potting materials show significant drift, including areas of shorting (i.e., complete failure of the wire to provide a useable signal), the line graph 362 associated with the potting material according to the present disclosure has a steady plot with limited drift.

Referring now to FIG. 9, shown therein is a graph 370 illustrating absolute 1-hour drift characteristics of an intravascular device using a potting material according to an embodiment of the present disclosure compared to absolute 1-hour drift characteristics of an intravascular device using an alternative potting material. The bar on the left side of the graph 370 illustrates the average drift per hour (mmHg/h) in distilled water at a temperature of 37° C. for the intravascular device using a potting material according to an embodiment of the present disclosure, in. particular Locate® 5248™, while the bar on the right side of the graph illustrates the average drift per hour (mmHg/h) in distilled water at a temperature of 37° C. tier the intravascular device using an alternative potting material, in particular an Ablebond® epoxy that is currently implemented in commercially available pressure-sensing guide wires. As shown, the average drift (mmHg/h) for the intravascular device using a potting material according to an embodiment of the present disclosure is significantly less than the currently used potting material. In particular, the currently used potting material results in a drift over ten times as large as the potting materials of the present disclosure, with the Loctite®

5248™ having an average drift of 0.79 mmHg/h with a standard deviation of ±0.52 mmHg compared to the Ablebond® epoxy having an average drift of 8.87 mmHg/h with a standard deviation of +4.63 mmHg.

Referring now to FIG. 10, shown therein is a graph 380 illustrating absolute initial offset characteristics of an intravascular device using a potting material according to an embodiment of the present disclosure compared to absolute initial offset characteristics of an intravascular device using an alternative potting material. The bar on the left side of the graph 370 illustrates the initial offset (mmHg) in distilled water at a temperature of 37° C. for the intravascular device using a potting material according to an embodiment of the present disclosure, in particular Loctite® 5248™, while the bar on the right side of the graph illustrates the initial offset (mmHg) in distilled water at a temperature of 37° C. for the intravascular device using an alternative potting material, in particular an Ablebond® epoxy that is currently implemented in commercially available pressure-sensing guide wires. As shown, the initial offset (mmHg) for the intravascular device using a potting material according to an embodiment of the present disclosure is significantly less than the currently used potting material and with less variation. In particular, the currently used potting material has an initial offset over three times as large as the potting materials of the present disclosure, with the Loctite® 5248™ having an initial offset of 0.48 mmHg/h with a standard deviation of ±0.74 mmHg compared to the Ablebond® epoxy having an initial offset of 1.60 mmHg with a standard deviation of ±2.44 mmHg.

Figure 11:
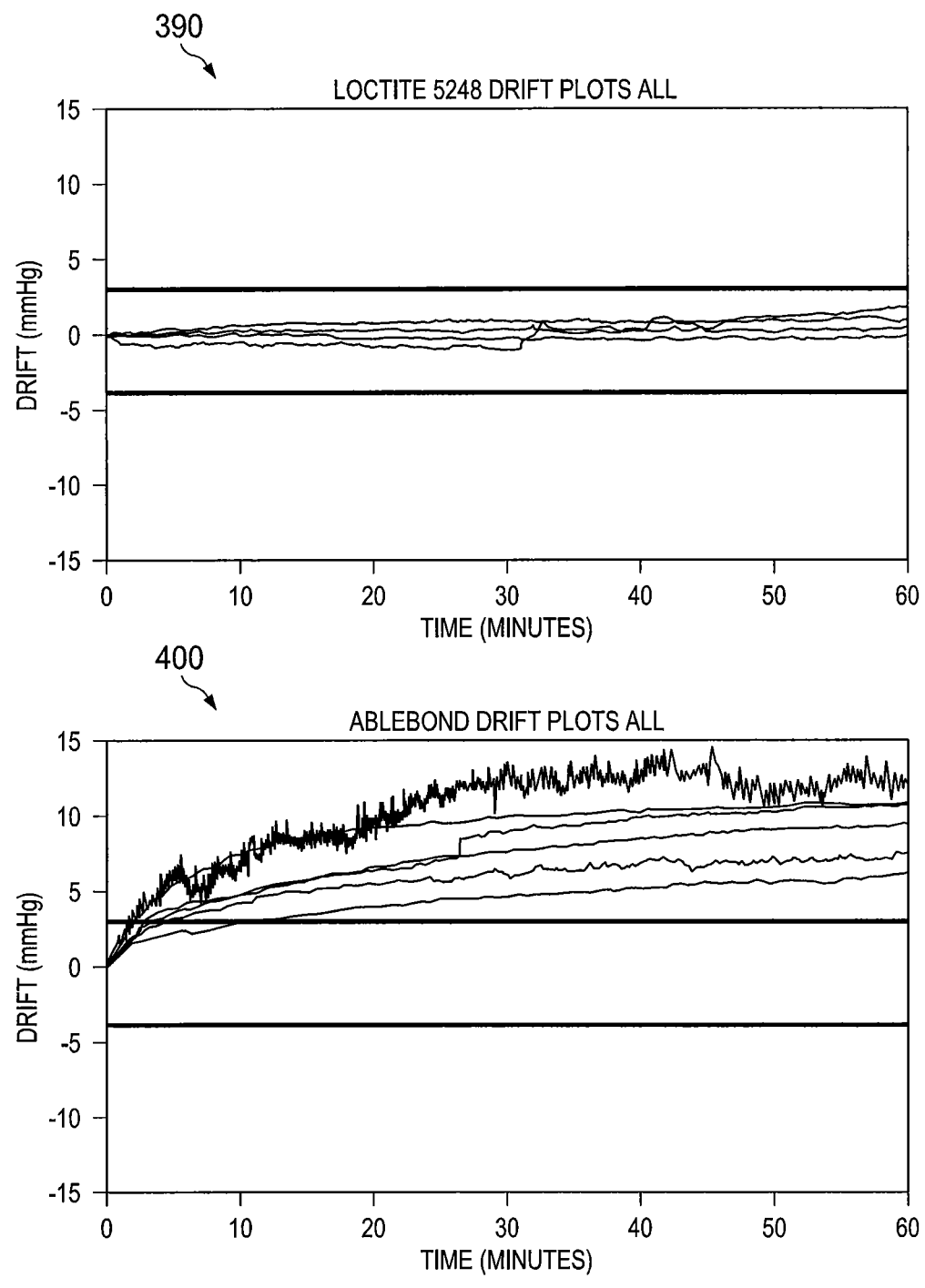
FIG. 11 is a pair of graphs illustrating the relative drift characteristics of an intravascular device using a potting material according to an embodiment of the present disclosure and an intravascular device using an alternative potting material.

Referring now to FIG. 11, shown therein are a pair of graphs 390, 400 illustrating the relative drift characteristics of an intravascular device using a potting material according to an embodiment of the present disclosure (graph 390) and an intravascular device using an alternative potting material (graph 400). In that regard, graph 390 illustrates the drift (mmHg) over time (min) in distilled water at a temperature of 37° C. for eight different intravascular devices with sensors implemented using a potting material according to an embodiment of the present disclosure, in particular Loctite® 5248™. On the other hand, graph 400 illustrates the drift (mmHg) over time (min) in distilled water at a temperature of 37° C. for eight different intravascular devices with sensors implemented using an alternative potting material, in particular an Ablebond® epoxy that is currently implemented in commercially available pressure-sensing guide wires. As shown, the drift of the intravascular device using a potting material according to an embodiment of the present disclosure is significantly less than the currently used potting material. Further, the drift of the intravascular device using a potting material according to an embodiment of the present disclosure has more consistency (i.e., less deviation) between runs relative to the currently used potting material.

Referring now to FIG. 12, shown therein is a graph 410 illustrating a maximum drift of an intravascular device using a potting material according to an embodiment of the present disclosure compared to a maximum drift of an intravascular device using an alternative potting material in a twenty minute animal study. The bar on the left side of the graph 410 illustrates the maximum drift (mmHg) over twenty minutes in an animal study for the intravascular device using a potting material according to an embodiment of the present disclosure, in particular Loctite® 5248™, while the bar on the right side of the graph illustrates the maximum drift (mmHg) over twenty minutes in an animal study for the intravascular device using an alternative potting material, in particular an Ablebond® epoxy that is currently implemented in commercially available pressure-sensing guide wires. As shown, the maximum drill (mmHg) for the intravascular device using a potting material according to an embodiment of the present disclosure is significantly less than the maximum drift of the currently used potting material. In particular, the currently used potting material results in a maximum drift over twenty times as large as the potting materials of the present disclosure in the twenty minute animal study, with the Loctite® 5248™ having an average maximum drift of 0.24 mmHg with a standard deviation of ±0.12 mmHg compared to the Ablebond® epoxy having an average maximum drift of 4.72 mmHg/h with a standard deviation of ±0.47 mmHg.

Referring now to FIG. 13, shown therein is a graph 420 illustrating drift characteristics of intravascular devices using a potting material according to an embodiment of the present disclosure compared to drift characteristics of intravascular devices using an alternative potting material in a twenty minute animal study. In that regard, the three line graphs identified as 422 illustrate the drift (mmHg) over time in an animal study for the intravascular device using an alternative potting material, while the three line graphs identified as 424 illustrate the drift (mmHg) over time in an animal study for the intravascular device using a potting material according to an embodiment of the present disclosure, in particular Loctite® 5248™. Consistent with the previous graphs, the intravascular device using a potting material according to the present disclosure has a substantially overall drift and less deviation between runs.

Referring now to FIG. 14, shown therein is a graph 430 illustrating drift characteristics of intravascular devices using a potting material according to an embodiment of the present disclosure in a one hour animal study. In that regard, the graph 430 shows that even over a full hour of in vivo use, the intravascular devices that use a potting material according to the present disclosure continue to have low overall drift with minimum deviation between wires and runs.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A guide wire, comprising:
  a flexible elongate body having a proximal portion, a distal portion, and a lumen extending along a length of the flexible elongate body between the proximal and distal portions;
  a sensor housing disposed at the distal portion of the flexible elongate body, wherein the sensor housing has a proximal portion and a distal portion;
  a pressure sensor within the distal portion of the sensor housing;
  a plurality of conductors electrically coupled to the pressure sensor and extending from the pressure sensor through the lumen to the proximal portion of the flexible elongate body;

a potting material within the distal portion of the sensor housing, the potting material covering electrical connections between the plurality of conductors and the pressure sensor, the electrical connections being at the distal portion of the sensor housing, wherein the potting material has a durometer hardness between about 20 Shore A and about 50 Shore A to minimize forces imparted on the pressure sensor; and an adhesive within the proximal portion of the sensor housing, wherein the adhesive is in contact with the plurality of conductors at the proximal portion of the sensor housing.

2. The guide wire of claim 1, wherein the potting material has a durometer hardness of approximately 25-30 Shore A.

3. The guide wire of claim 1, wherein the potting material has a moisture absorption rate of about 0% per twenty-four hours.

4. The guide wire of claim 1, wherein the potting material is a UV-cured potting material.

5. The guide wire of claim 4, wherein the UV-cured potting material includes a secondary humidity cure.

6. The guide wire of claim 1, wherein the potting material has a linear shrinkage of 0%.

7. The guide wire of claim 1, wherein the potting material has a coefficient of thermal expansion (m/m/-° C.) of between about $1.0 \times 10^{-5}$ and about $5.0 \times 10^{-4}$.

8. The guide wire of claim 7, wherein the potting material has a coefficient of thermal expansion (m/m/-° C.) of about $2.89 \times 10^{-4}$.

9. The guide wire of claim 1, wherein the potting material has a volume resistivity (Ω-cm) between about $6.0 \times 10^{13}$ and about $1.0 \times 10^{14}$.

10. The guide wire of claim 9, wherein the potting material has a volume resistivity (Ω-cm) of about $8.3 \times 10^{13}$.

11. The guide wire of claim 1, further comprising a first flexible element extending distally from the sensor housing and a second flexible element extending proximally from the sensor housing.

12. The guide wire of claim 11, wherein at least one of the first and second flexible elements comprises a coil.

13. The guide wire of claim 12, wherein at least one of the first and second flexible elements comprises a polymer tubing.

14. The guide wire of claim 1, wherein the sensor housing comprises a further lumen, wherein the potting material partially fills the further lumen at the distal portion of the sensor housing, and wherein the adhesive completely fills the further lumen at the proximal portion of the sensor housing.

15. The guide wire of claim 1, further comprising a further adhesive in contact with the sensor and the sensor housing, the further adhesive longitudinally overlapping the potting material at the distal portion of the sensor housing and the adhesive at the proximal portion of the sensor housing.

* * * * *